United States Patent
Kahale et al.

(10) Patent No.: US 6,271,260 B1
(45) Date of Patent: Aug. 7, 2001

(54) PREVENTION/RETARDATION OF HAIR GROWTH

(76) Inventors: Laura Kahale, 70 Mountford Avenue, Guildford, New South Wales 2161; Malcolm Nearn, 3 Riverview Road, Kentlyn, New South Wales 2560, both of (AU)

(*) Notice: Subject to any disclaimer, the term of this patent is extended or adjusted under 35 U.S.C. 154(b) by 0 days.

(21) Appl. No.: 09/424,165

(22) PCT Filed: May 20, 1998

(86) PCT No.: PCT/AU98/00374

§ 371 Date: Dec. 6, 1999

§ 102(e) Date: Dec. 6, 1999

(87) PCT Pub. No.: WO98/52515

PCT Pub. Date: Nov. 26, 1998

(30) Foreign Application Priority Data

May 20, 1997 (AU) .................................................. P06902

(51) Int. Cl.$^7$ .................................................. A61K 31/19
(52) U.S. Cl. ........................... 514/574; 514/880; 424/663
(58) Field of Search ................................... 514/574, 880; 424/663

(56) References Cited

U.S. PATENT DOCUMENTS

| | | | |
|---|---|---|---|
| 4,253,993 | 3/1981 | Ramsey, III et al. | 252/548 |
| 4,321,156 | 3/1982 | Bushman | 252/142 |
| 4,720,489 | 1/1988 | Shander | 514/171 |
| 4,885,289 | 12/1989 | Breuer et al. | 514/170 |
| 5,095,007 | 3/1992 | Ahluwalia | 514/23 |
| 5,096,911 | 3/1992 | Ahluwalia et al. | 514/380 |
| 5,100,656 | 3/1992 | Lang et al. | 424/70 |
| 5,132,293 | 7/1992 | Shander et al. | 514/46 |
| 5,143,925 | 9/1992 | Shander et al. | 514/378 |
| 5,455,234 | 10/1995 | Ahluwalia et al. | 514/46 |

FOREIGN PATENT DOCUMENTS

| | | |
|---|---|---|
| 895839 | 3/1972 | (CA) . |
| 0 182 369 A2 | 5/1986 | (EP) . |
| 0 532 219 A2 | 3/1993 | (EP) . |
| 0 532 219 A3 | 3/1993 | (EP) . |
| 0 739 621 A1 | 10/1996 | (EP) . |
| 94/27586 | 12/1994 | (WO) . |

OTHER PUBLICATIONS

Derwent Abstract Accession No. 90–296104/39, Class D21, SU 1528–494–A (CHEM IND RES DES) Dec. 15, 1989.

M. Gamez–Garcia "Effects of some oils, emulsions, and other aqueous systems on the mechanical properties of hair at small deformations", J. Soc. Cosmet. Chem., 44, 69–87 (Jan./Feb. 1993).

*Primary Examiner*—Rebecca Cook
(74) *Attorney, Agent, or Firm*—Gifford, Krass, Groh, Sprinkle, Anderson & Citkowski, P.C.

(57) ABSTRACT

A composition and method for retarding or preventing hair growth, wherein the composition includes a) citric acid, b) an electrolyte, and c) a cosmetically acceptable aqueous vehicle which includes a film forming agent.

8 Claims, No Drawings

PREVENTION/RETARDATION OF HAIR GROWTH

This is a 371 of PCT/AU98/00374 filed May 20, 1998.

TECHNICAL FIELD

The present invention relates to a composition and method for the retardation or prevention of hair growth.

BACKGROUND ART

In the past, there has been great emphasis on methods and compositions relating to the inhibition of unwanted hair growth in humans. In particular, for cosmetic reasons it is desirable to remove unwanted hair from parts of the body such as the legs, armpits and face without recourse to shaving.

The products that are currently available for topical use in the removal of unwanted hair are mostly based on thioglycollates as the active ingredient. Examples of products containing thioglycollates are available under the trade names "VEET" and "NAIR". Thioglycollates function as reducing agents at high pH by reducing disulfide bonds in hair. Following penetration into the follicular canal. the hair is weakened in the region above the keratinizing zone. The hair shaft may then be broken off just below the skin surface leaving a soft, smooth skin surface.

Hair growth does not however cease and, since the hair is broken near the surface, regrowth occurs within a relatively short time and the cosmetic advantage is thus rapidly lost. Retreatment with the thioglycollate product is necessary if the treated skin is to be maintained in a hairless condition. There is consumer resistance to the continual use of thioglycollate hair removal product as skill irritation is sometimes encountered. However, as no alternative methods of hair removal exist apart from shaving and plucking (including the use of tweezers, forceps and waxing) of individual hairs, in the past thioglycollate-containing products have offered the most effective method. particularly for women, for the removal of unwanted hair from the body surface.

The present inventors have surprisingly found a method and a composition which when applied topically to the skin retards or prevents hair growth. The inventors have found that the method and composition cause the hair growth to be finer, thinner, shorter and much less visible. Typically, coarse hair is replaced by vellus hair. With repeated application the inventors of the present invention have found that hair growth may be prevented entirely.

DISCLOSURE OF INVENTION

In a first aspect, the present invention consists in a composition for retarding or preventing hair growth including:
(a) citric acid:
(b) an electrolyte; and
(c) a cosmetically acceptable aqueous vehicle which includes a film forming agent.

In a second aspect, the present invention consists in a method for retarding and/or preventing hair growth comprising applying a composition which includes:
(a) citric acid;
(b) an electrolyte; and
(c) a cosmetically acceptable aqueous vehicle which includes a film forming agent;
to an area of skin in which hair growth occurs and allowing the composition to contact the skin for a time sufficient so as to effectively prevent or retard hair growth.

In a third aspect. the present invention is directed to the use of a composition as defined in the first aspect of the invention for preventing or retarding hair growth.

The concentration of citric acid may be greater than 30% w/w. Preferably, the concentration of citric acid will be in the range of 1 to 30% w/w and more preferably 5 to 20% w/w.

The electrolyte may be selected from a variety of compounds including alkali metal and alkali earth metal salts that are water soluble. Preferably the electrolyte is sodium chloride and more preferably Dead Sea Salt. The electrolyte may be present in a concentration of greater than 20% w/w. Preferred concentrations of electrolyte are in the range of 1 to 20% w/w and more preferably 5 to 10% w/w.

The cosmetically acceptable aqueous vehicle acts as a diluent, dispersant or carrier for other materials present in the composition, so as to facilitate the distribution of the composition when applied to the relevant area of skin. Suitable vehicles include emulsions, microemulsions or an aqueous solution or dispersion of a film forming agent.

The film forming agent may be selected from a variety of ingredients including liquid or solid emollients, emulsifiers, surface active agents, gums, humectants, thickeners, powders and protein solutions. These agents can be used singly or as mixtures of one or more agents. Preferably the film forming agent is present in a concentration in the range of 0.05 to 40% w/w.

Emollients, such as mineral oil, fatty alcohols, alkyl esters, silicones and silicone derivatives may be employed in the present invention. Fatty alcohols may be selected from stearyl alcohol and cetyl alcohol. Alkyl esters may be selected from octyl palmitate, decyl oleate and isopropyl myristate. Silicones and silicone derivatives may be selected from phenyl dimethicone, dimethicone and simethicone. It will be appreciated, however, that the present invention is not limited to the aforementioned emollients.

The composition of the present invention may optionally comprise one or more emulsifiers/surface active agents, the choice of which will normally determine whether a water-in-oil emulsion or an oil-in-water emulsion is formed. Emulsions preferably contain 3.0 to 10% w/w of emulsifiers and more preferably 0.5 to 15% w/w. Microemulsions preferably contain 0.5 to 35% w/w of surface active agents and more preferably 15 to 28% w/w.

Emulsifiers, such as mixtures of glyceryl stearate and PEG-100 stearate (Lipomulse 165 and Arlacel 165), Tegocare PS (methyl glucose sesquistearate), PEG7 hydrogenated castor oil (Arlacel 989) and glyceryl sorbitan oleostearate (Arlacel 481) can be employed in the present invention. It will be appreciated, however, that the present invention is not limited to the aforementioned emulsifiers.

Surface active agents for microemulsions may be selected from Lipocol SC20 (Ceteareth-20), Ameroxol OE20 (Oleth-20), Lipocol L4 (Laureth-4), Amerchol L101 (Lanolin alcohol and mineral oil), Cetiol HE (PEG 7 glyceryl cocoate) and Liponic EG1 (Glycereth-20). It will be appreciated, however, that the present invention is not limited to the aforementioned surface active agents.

The composition of the present invention may be preserved by humectants which act as water activity depressants. Humectants such as glycerol and polyethylene glycols may be employed in the present invention. Preferably, the humectant is present in a concentration of between 1 to 5% w/w. It will be appreciated, however, that the present invention is not limited to the aforementioned humectants.

A variety of gums including Sclerotium gum (Amigel) may be used in the present invention. Amigel is an effective polymer film forming agent and is preferably present in a concentration of 0.1 to 2% w/w.

Powders such as clays, silicas, talc and starch may be employed in the present invention. A variety of clays may be used including bentone. Silicas are preferably fumed silicas.

A variety of protein solutions may be used including beer.

It will be appreciated, however, that the present invention is not limited to the aforementioned electrolytes and film forming agents.

The composition according to the present invention may optionally comprise one or more conventional antiperspirant or deodorant active substances. Compositions according to the present invention can thus be used regularly on the underarm not only to prevent unwanted hair growth but also to reduce or eliminate perspiration and/or to reduce or eliminate malodour. Examples of conventional antiperspirant actives include astringent metallic salts such as aluminium chloride, aluminium chlorohydrate and zirconium chlorohydrate. A suitable deodorant is triclosan (Irgasan DP 300).

The pH of the composition of the present invention is preferably below 4.

The composition of the present invention may take the form of a cream, lotion, gel or spray.

The composition of the present invention may be topically applied to a selected area of the body in which it is desired to inhibit hair growth. For example, the composition can be applied to the face, neck, upper lip, chin, legs, arms, torso and armpits.

According to the method of the present invention, the time sufficient to effectively prevent or retard hair growth is at least 30 minutes per application. Preferably, the time sufficient to effectively prevent or retard hair growth is 4 h to 12 h per application.

Preferably, the composition is applied to all area of skill which has previously been subjected to mechanical depilation such as waxing or shaving or chemical depilation. In that case, the time sufficient to effectively prevent or retard hair growth is at least 5 minutes per application. Preferably, the time sufficient to effectively prevent of retard hair growth is 4 h to 12 h per application.

The composition is preferably applied to and left on an area of skin three times a week, preferably daily and even more preferably twice daily. Preferably, the composition once applied to the skin is not specifically removed but may be removed during daily washing rituals. Reduction of hair growth is demonstrated when the frequency or hair removal is reduced or the subject perceives less hair on the treated site or quantitatively, when the weight of hair removed by shaving (that is hair mass) is reduced.

It will be appreciated, however, that the time sufficient to prevent or retard hair growth may vary outside the preferred times depending on factors such as, the individuals volume of hair, genetic make up, frequency of washing etc.

MODES FOR CARRYING OUT THE INVENTION

The following examples illustrate compositions in accordance with the first aspect of the invention, which are suitable for topical application to an area of skin for retardation/prevention of hair growth in accordance with the second aspect of the present invention.

EXAMPLE 1

| Ingredients | % w/w |
| --- | --- |
| Sodium chloride | 3.0 |
| Citric acid | 10.0 |
| Lipomulse 165 | 0.5 |
| Amigel | 0.6 |
| Propylene glycol | 3.0 |
| Water | to 100 |

The citric acid and sodium chloride were dissolved in water with heating and stirring. Lipomulse 165 was added and the solution heated to 50° C. and stirred to disperse the Lipomulse 165. A paste of Amigel and propylene glycol was slowly added to the water solution with stirring. Care was taken not to create a turbulence during mixing so as to avoid aeration. The resulting solution was cooled to room temperature and the composition was obtained as a translucent lotion.

EXAMPLES 2, 3, 4

| Ingredients | Example 2 % w/w | Example 3 % w/w | Example 4 % w/w |
| --- | --- | --- | --- |
| Citric acid | 22.0 | 22.0 | 22.0 |
| Dead sea salt | 6.2 | 6.2 | 6.2 |
| Lipomulse 165 | 0.5 | 0.5 | 0.5 |
| Amigel | 0.6 | 1.2 | 2.4 |
| Propylene glycol | 3.0 | 3.0 | 3.0 |
| Water | to 100 | to 100 | to 100 |

The procedure outlined for Example 1 was employed to make the compositions according to Examples 2, 3 and 4. Example 2 was obtained as a lotion, Example 3 as a soft gel and Example 4 as a firm gel. Example 2 retained its viscosity and emulsion stability for at least 2 months at 45° C.

EXAMPLE 5

| Ingredients | % ww |
| --- | --- |
| Tegocare PS | 4.0 |
| Octyl Palmitate | 8.5 |
| Decyl Oleate | 8.5 |
| Arlacel 165 | 2.0 |
| Stearyl Alcohol | 2.0 |
| Glycerol | 2.0 |
| Water | 54.4 |
| Citric Acid | 10.0 |
| NaCl or Dead Sea Salt | 5 |
| Sodium Hydroxide to pH 3.5 | to 100 |

Tegocare PS, octyl palmitate, decyl oleate, Arlacel 165 and stearyl alcohol were combined and heated to 80° C. This solution was added to a mixture of glycerol and water at a temperature of 80°. The combined solution were mixed at a low speed with a mechanical stirrer. The resulting solution was cooled to 35 to 40° and a mixture of water, citric acid and sodium hydroxide added. The solution was cooled to room temperature and the composition according to Example 5 was obtained as an opaque oil in a water emulsion. The final product was obtained as a white lotion.

Ingredient Availability

| Ingredients | Chemical Name | Available from: |
|---|---|---|
| Citric Acid | — | Ajax Chemicals |
| Sodium chloride | — | Ajax Chemicals |
| Dead sea salt | — | Alban Huller Int |
| Sodium Hydroxide | — | ICI Australia |
| Mineral oil | | Exxon |
| Cetyl alcohol | — | Lipo-Australian agents Bronson and Jacobs P/L |
| Stearyl alcohol | — | Lipo-Australian agents Bronson and Jacobs P/L |
| Octyl palmitate | | Stepan |
| Decyl oleate | — | Goldschmidt |
| Phenyl dimethicone | — | Dow Corning |
| Dimethicone | — | Dow Corning |
| Simethicone | — | Dow Corning |
| Arlacel 165 | mixture of glyceryl stearate and PEG-100 stearate | Lipo-Australian agents Bronson and Jacobs P/L |
| Lipomulse 165 | mixture of glyceryl stearate and PEG-100 stearate | Lipo-Australian agents Bronson and Jacobs P/L |
| Arlacel 989 | PEG-7 hydrogenated castor oil | ICI Australia |
| Arlacel 481 | glyceryl sorbitan oleostearate | ICI Australia |
| Tegocare PS | Methyl Glucose sesquistearate | Goldschmidt |
| Lipocol SC20 | Ceteareth-20 | Lipo-Australian agents Bronson and Jacobs P/L |
| Ameroxol OE20 | Oleth-20 | Amerchol-Australian agents Bronson and |
| Lipocol L4 | Laureth-4 | Lipo-Australian agents Bronson and Jacobs P/L |
| Amerchol L101 | Lanolin alcohol and mineral oil | Amerchol-Australian agents Bronson and |
| Cetiol HE | PEG-7 glyceryl cocoate | Henkel Australia |
| Liponic EG1 | Glycereth-20 | Lipo-Australian agents Bronson and Jacobs P/L |
| Glycerol | — | Unichema |
| Polyethylene glycol | — | Stepan |
| Amigel | Sclerotium gum | Alban Muller Int. |
| Aluminium chloride | — | Bronson and Jacobs P/L |
| Aluminium chlorohydrate | — | Bronson and Jacobs P/L |
| Zirconium chlorohydrate | — | Bronson and Jacobs P/L |
| Irgasan DP 300 | Triclosan | Ciba-Geigy Australia Ltd |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for retarding or preventing hair growth comprising applying a composition comprising:

(a) citric acid;

(b) an electrolyte; and (c) a cosmetically acceptable aqueous vehicle which includes a film forming agent;

in an amount effective for retarding or preventing hair growth.

2. The method according to claim 1 wherein the time sufficient to effectively prevent or retard hair growth is at least 30 minutes per application.

3. The method according to claim 2 wherein the time sufficient to effectively prevent or retard hair growth is 4 hours to 12 hours per application.

4. The method according to claim 1 wherein the area of skin has previously been subjected to depilation.

5. The method according to claim 4 wherein the area of skin has been subjected to chemical depilation.

6. The method according to claim 4 wherein the area of skin has been subjected to mechanical depilation.

7. The method according to claim 6 wherein the time sufficient to effectively prevent or retard hair growth is at least 5 minutes per application.

8. The method according to claim 7 wherein the time sufficient to effectively prevent or retard hair growth is 4 hours to 12 hours per application.

\* \* \* \* \*

UNITED STATES PATENT AND TRADEMARK OFFICE
CERTIFICATE OF CORRECTION

PATENT NO. : 6,271,260 B1
DATED : August 7, 2001
INVENTOR(S) : Laura Kahale et al.

It is certified that error appears in the above-identified patent and that said Letters Patent is hereby corrected as shown below:

<u>Title page,</u>
Item [54], replace "PREVENTION/RETARDATION OF HAIR GROWTH" with
-- A COMPOSITION AND METHOD FOR RETARDING HAIR GROWTH --

<u>Column 1,</u>
Line 35, replace "skill" with -- skin --.

<u>Column 2,</u>
Line 1, replace "." with -- , --.

<u>Column 3,</u>
Line 36, replace "all" with -- an --.
Line 36, replace "skill" with -- skin --.

<u>Column 4,</u>
Line 16, after "C" delete -- . --.

<u>Column 6,</u>
Line 22, after "growth" insert -- to an area of the skin which hair growth occurs and allowing the composition to contact the skin for a time sufficient as to effectively prevent or retard hair growth --.

Signed and Sealed this

Thirtieth Day of July, 2002

*Attest:*

JAMES E. ROGAN
*Attesting Officer*   *Director of the United States Patent and Trademark Office*